(12) United States Patent
Millefanti et al.

(10) Patent No.: US 9,403,742 B2
(45) Date of Patent: Aug. 2, 2016

(54) PROCESS FOR THE SYNTHESIS OF TRIFLUOROETHYLENE

(71) Applicant: SOLVAY SPECIALTY POLYMERS ITALY S.P.A., Bollate (IT)

(72) Inventors: Stefano Millefanti, Como (IT); Vito Tortelli, Milan (IT); Giuseppe Marchionni, Milan (IT)

(73) Assignee: SOLVAY SPECIALTY POLYMERS ITALY S.P.A., Bollate (Milano) (IT)

( * ) Notice: Subject to any disclaimer, the term of this patent is extended or adjusted under 35 U.S.C. 154(b) by 0 days.

(21) Appl. No.: 14/310,230

(22) Filed: Jun. 20, 2014

(65) Prior Publication Data

US 2014/0303411 A1    Oct. 9, 2014

Related U.S. Application Data

(62) Division of application No. 13/704,001, filed as application No. PCT/EP2011/060400 on Jun. 22, 2011, now abandoned.

(30) Foreign Application Priority Data

Jul. 1, 2010 (EP) .................................. 10168130

(51) Int. Cl.
| | |
|---|---|
| *C08F 12/20* | (2006.01) |
| *C08F 14/24* | (2006.01) |
| *C08F 114/24* | (2006.01) |
| *C08F 214/24* | (2006.01) |
| *C07C 17/23* | (2006.01) |
| *B01J 21/18* | (2006.01) |
| *B01J 23/42* | (2006.01) |
| *B01J 23/44* | (2006.01) |
| *B01J 37/00* | (2006.01) |
| *B01J 37/18* | (2006.01) |

(52) U.S. Cl.
CPC ................. *C07C 17/23* (2013.01); *B01J 21/18* (2013.01); *B01J 23/42* (2013.01); *B01J 23/44* (2013.01); *B01J 37/0009* (2013.01); *B01J 37/18* (2013.01)

(58) Field of Classification Search
CPC ............ B01J 21/18; B01J 23/42; B01J 23/44; C07C 21/18; C08F 12/20; C08F 14/24; C08F 114/24; C08F 214/24
USPC .............................. 570/156; 526/249; 502/185
See application file for complete search history.

(56) References Cited

U.S. PATENT DOCUMENTS

| | | | | |
|---|---|---|---|---|
| 2,802,887 | A * | 8/1957 | Smith et al. ................... | 570/156 |
| 3,564,064 | A * | 2/1971 | Nakagawa et al. ........... | 570/156 |
| 5,053,377 | A * | 10/1991 | Lerot et al. .................... | 502/226 |
| 5,089,454 | A * | 2/1992 | Lerot et al. .................... | 502/226 |
| 5,118,888 | A * | 6/1992 | Gervasutti et al. ............ | 570/153 |
| 5,283,379 | A * | 2/1994 | Saiki et al. .................... | 570/156 |
| 5,315,045 | A * | 5/1994 | Berthe et al. .................. | 570/153 |
| 2006/0217577 | A1 * | 9/2006 | Mukhopadhyay et al. ... | 570/156 |

FOREIGN PATENT DOCUMENTS

| | | | | |
|---|---|---|---|---|
| JP | 62-252736 | * | 11/1987 | ............. C07C 21/18 |
| WO | WO 2012000853 A1 | * | 1/2012 | |

* cited by examiner

*Primary Examiner* — Patricia L Hailey

(57) ABSTRACT

A catalytic process for the synthesis of trifluoroethylene from chlorotrifluoroethylene which comprises contacting chlorotrifluoroethylene with hydrogen in the presence of a catalyst consisting of palladium or platinum supported on extruded activated carbon.

6 Claims, No Drawings

PROCESS FOR THE SYNTHESIS OF TRIFLUOROETHYLENE

This application is a divisional application of U.S. application Ser. No. 13/704,001, filed Dec. 13, 2012, which is a U.S. national stage entry under 35 U.S.C. §371 of International Application No. PCT/EP2011/060400 filed Jun. 22, 2011, which claims priority to European application No. 10168130.2 filed on Jul. 1, 2010. The entire contents of these applications are explicitly incorporated herein by this reference.

TECHNICAL FIELD

The present invention relates to a catalytic process for the synthesis of trifluoroethylene. In particular the invention relates to a process for the synthesis of trifluoroethylene by reaction of chlorotrifluoroethylene with hydrogen in the presence of a heterogeneous catalyst.

BACKGROUND ART

The hydrodechlorination of chlorotrifluoroethylene to yield trifluoroethylene has been previously described.

Mention can be made of U.S. Pat. No. 2,802,887 (ALLIED CHEMICAL) Aug. 13, 1957 which discloses the gas-phase reaction of chlorotrifluoroethylene with hydrogen to produce trifluoroethylene in the presence of a catalyst comprising palladium supported on activated carbon. The reaction however proceeds with both low conversion of chlorotrifluoroethylene and low yield in trifluoroethylene.

U.S. Pat. No. 3,564,064 Feb. 16, 1971 discloses the catalytic gas-phase reaction of chlorotrifluoroethylene with hydrogen to produce trifluoroethylene in the presence of a catalyst comprising palladium or platinum supported on activated carbon. This process may proceed with high conversion of chlorotrifluoroethylene but with a parallel reduction in the yield of trifluoroethylene.

In consideration of the high cost of chlorotrifluoroethylene it would be desirable to have available a process capable of maximizing the conversion of chlorotrifluoroethylene without compromising the overall yield in trifluoroethylene thereby increasing the profitability of the process.

DISCLOSURE OF INVENTION

It has now been found that when using a supported platinum or palladium catalyst wherein the support for the noble metal is a specific form of activated carbon the reaction of chlorotrifluoroethylene with hydrogen proceeds with a high conversion of chlorotrifluoroethylene and without concurrently decreasing the selectivity towards the formation of trifluoroethylene. The advantages in productivity can be obtained even at low concentrations of the noble metal on the support and by working with a high dilution of chlorotrifluoroethylene by operating the process in the presence of an inert gas.

A first object of the present invention is a process for preparing trifluoroethylene comprising contacting chlorotrifluoroethylene with hydrogen in the presence of a catalyst consisting of palladium or platinum supported on activated carbon, in which the activated carbon is extruded activated carbon.

A second object is a catalyst for the hydrodechlorination of chlorotrifluoroethylene, said catalyst consisting of palladium or platinum supported on activated carbon, characterized in that the activated carbon is extruded activated carbon.

The term "activated carbon" is generally used to collectively refer to processed carbonaceous materials characterized by a porous structure and a large internal surface area, generally comprised between 500 and 1500 $m^2/g$. Activated carbon is obtained on a commercial scale from carbon containing raw materials, e.g. wood, peat, coconut shells, by chemical or gas activation. Activated carbon is commercially available in different forms, namely granular, powdered or extruded form.

Extruded activated carbon is typically obtained from finely powdered raw materials by mixing with a suitable binder followed by extrusion, to form pellets or strands which are then cut into pieces. The pellets are then chemically activated or carbonized and finally gas activated. Typical extruded activated carbons have a pellet diameter in the range of 0.8 to 130 mm.

Suitable extruded activated carbons for the process of the invention are available commercially for instance from Norit Nederland B.V., Degussa AG, Calgon Carbon Corporation.

The process of the invention is preferably carried out in the gas-phase. In an embodiment of the inventive process a gaseous stream of hydrogen and chlorotrifluoroethylene is fed to the reaction zone and brought into contact with the catalyst held at a suitable temperature. The produced trifluoroethylene is recovered from the effluent gas. The reaction products and any unreacted starting material may be recovered and isolated by conventional methods. The main by-product of the process has been identified to be $CH_2FCHF_2$.

The molar ratio between the hydrogen and the chlorotrifluoroethylene fed to the reaction zone is typically comprised between 0.75:1 and 1.25:1, preferably between 0.9:1 and 1.1:1.

An inert gas may be optionally mixed with hydrogen and chlorotrifluoroethylene. Suitable inert gases are for instance nitrogen, helium, argon. Preferably the inert gas is nitrogen. The use of an inert gas in the process allows to better control the temperature of the exothermic reaction preventing local overheating of the catalyst bed and of the reactor, thus increasing productivity.

Additionally, the inert gas may serve as a diluent to reduce the concentration of the reactants and/or the products below the point where they form flammable mixtures.

The concentration of chlorotrifluoroethylene in the gaseous stream fed to the reaction zone is conveniently comprised between 5 and 55% by volume, preferably between 10 and 50% by volume.

The reaction pressure is not critical to the process. Generally the process is carried out at pressure of from 0.01 MPa to 0.5 MPa, preferably at a pressure of from about 0.05 MPa to 0.2 MPa.

The reaction may be conducted at any suitable temperature, generally at a temperature in the range of from 100° C. to 350° C., preferably in the range of from 150° C. to 300° C., and more preferably in the range of from 200° C. to 250° C.

The reaction contact time for the reactants may be any suitable contact time, usually a time of from 0.1 second to 100 seconds, preferably from 0.1 second to 60 seconds, and more preferably from 0.5 second to 30 seconds.

Any suitable space velocity of the reactants may be employed. For instance, in the case of chlorotrifluoroethylene the space velocity can be in the range from 0.2 to 50 $gCTFE*h^{-1}*g_{cat}^{-1}$, preferably from 1 to 40 $gCTFE*h^{-1}*g_{cat}^{-1}$ and more preferably from 2 to 30 $gCTFE*h^{-1}*g_{cat}^{-1}$.

The process may be conducted in any suitable reaction vessel. The reaction vessel should be constructed of materials which are inert towards the reactants as well as the products, such as for example, Hastelloy, Inconel, Monel, stainless steel vessels. Preferably the process is carried out in a tubular stainless steel reactor, provided with suitable means to maintain the required temperature inside the reactor.

The catalyst used in the process consists of platinum or palladium supported on extruded activated carbon. Preferably the catalyst consists of palladium supported on extruded activated carbon.

The amount of metal supported on the extruded activated carbon is typically comprised between 0.05 and 5% by weight, preferably between 0.1 and 4% by weight, more preferably between 0.2 and 3% by weight, and even more preferably between 0.3 and 2.5% by weight.

The catalyst may be prepared by conventional methods, such as the incipient wetness impregnation method. In such a method an aqueous solution of a suitable metal precursor is added to the support, dried, followed by reduction of the metal. Among suitable precursors mention can be made of $PdCl_2$, $Pd(NO_3)_2$, $H_2PtCl_4$.

Should the disclosure of any of the patents, patent applications, and publications that are incorporated herein by reference conflict with the present description to the extent that it might render a term unclear, the present description shall take precedence.

The invention is illustrated by the following illustrative, but non-limiting examples.

EXAMPLES

Materials

NORIT® RX3 EXTRA (Norit Nederland B.V.) extruded activated carbon having BET area of 1400 $m^2/g$ NORIT® GCN 1240 (Norit Nederland B.V.) granular activated carbon having BET area of 1300 $m^2/g$ Methods General Catalyst Preparation Procedure The activated carbon as received from the supplier was crushed and sieved in order to obtain granules with a diameter of 0.5-1 mm. The granules were dried under vacuum at 200° C. and then impregnated with incipient wetness method with an aqueous hydrochloridric solution of $PdCl_2$ to obtain different concentrations of palladium on the support.

Catalyst Activation:

Each catalyst was dried under a nitrogen flow at 300° C. for 6 h and then reduced in a $H_2/N_2$ stream (5% by volume $H_2$) from room temperature to 350° C. with thermal ramp of 5° C./min. After 30 minutes at 350° C. hydrogen concentration was raised to 10% by volume and kept for 30 minutes, followed by a treatment with a hydrogen concentration of 50% by volume for 4 h. At the end of the treatment the catalyst was cooled at room temperature and characterized to determine the effective concentration of palladium.

General Procedure for the Catalytic Tests

A sample of catalyst was loaded in a stainless steel AISI 316 down-flow tubular reactor (length=52 cm, internal diameter=10 mm). Quartz granules were positioned above and below the catalyst bed to assure the pre-heating of the gas mixture and to support the catalyst bed. Before each run the catalyst was dried at 350° C. for 4 h and reactivated following the activation procedure described above. The temperature was lowered to the reaction temperature, the reactants and the inert gas, when present, were fed to the catalyst bed. The effluent stream was analysed to determine the composition of the product mix (yield and selectivity).

Example 1

Following the general catalyst preparation procedure described above two catalyst were prepared using the extruded activated carbon NORIT® 3X EXTRA as the support and having different concentrations of palladium, as shown in Table 1.

TABLE 1

| Catalyst | Pd (% wt) |
|---|---|
| A | 1.14 |
| B | 0.51 |

2.0 g of each catalyst was loaded into the reactor and tested according to the general procedure described above. The molar ratio $H_2$/chlorotrifluoroethylene was 1:1 and the temperature was set at 200° C. The reaction was carried out in the presence of nitrogen, the final concentration of chlorotrifluoroethylene in the gaseous stream for each run is reported in Table 2. The effluent gas from the reactor was analysed to determine the conversion of chlorotrifluoroethylene (CTFE) and the selectivity in trifluoroethylene (TrFE). The results reported in Table 2 below, show that the process proceeds with very high CTFE conversion rates and with high selectivity in TrFE. Furthermore, reducing the concentration of CTFE from 33 to 11% by volume does not affect the conversion and the selectivity of the process (Run 1 and 2).

TABLE 2

| Run | Catalyst | CTFE (vol %) | Space velocity (g/h *CTFE * gcat-1) | Residence time (sec) | Conversion CTFE (%) | Selectivity TrFE (%) |
|---|---|---|---|---|---|---|
| 1 | A | 33 | 2.6 | 4.2 | 93 | 71 |
| 2 | A | 11 | 2.6 | 1.5 | 93 | 75 |
| 3 | B | 33 | 2.6 | 4.2 | 98 | 70 |

Example 2 and Comparative Example 1

Following the general catalyst preparation procedure described above one catalyst was prepared using the granular activated carbon NORIT® GCN 1240 as the support and having a palladium concentration of 1.17% by weight (Catalyst C).

0.5 g of catalyst A and C were loaded into the reactor and tested according to the general procedure described above. The molar ratio $H_2$/chlorotrifluoroethylene was 1:1 and the temperature was set at 200-230° C. The reaction was carried out in the presence of nitrogen, the final concentration of chlorotrifluoroethylene in the gaseous stream for each run is reported in Table 3. The effluent gas from the reactor was analysed to determine the conversion of chlorotrifluoroethylene (CTFE) and the selectivity in trifluoroethylene (TrFE).

TABLE 3

| Run | Catalyst | CTFE (vol %) | Space velocity (g/h *CTFE * gcat-1) | Residence time (sec) | Conversion CTFE (%) | Selectivity TrFE (%) |
|---|---|---|---|---|---|---|
| 4 | A | 30 | 3.6 | 1.5 | 93 | 79 |
| 5 | A | 33 | 13.9 | 0.4 | 91 | 82 |
| 6 | A | 34 | 29.5 | 0.2 | 83 | 80 |
| 7 | C | 29 | 3.6 | 1.5 | 82 | 73 |

TABLE 3-continued

| Run | Catalyst | CTFE (vol %) | Space velocity (g/h *CTFE * gcat-1) | Residence time (sec) | Conversion CTFE (%) | Selectivity TrFE (%) |
|---|---|---|---|---|---|---|
| 8 | C | 32 | 13.5 | 0.4 | 80 | 73 |
| 9 | C | 33 | 29.9 | 0.2 | 71 | 72 |

The reported in Table 3 above (runs 4-6 vs. runs 7-9), show that using extruded activated carbon as the catalyst support, rather than a granular activated carbon, provides a higher conversion of CTFE, all the other process parameters being the same.

The invention claimed is:

1. A process for preparing trifluoroethylene, the process comprising contacting chlorotrifluoroethylene with hydrogen in the presence of a catalyst consisting of palladium or platinum supported on activated carbon, wherein the activated carbon is extruded activated carbon.

2. The process according to claim 1 wherein the catalyst consists of the palladium supported on the extruded activated carbon.

3. The process according to claim 1, wherein the process is carried out in a gas-phase by contacting a gaseous stream of the chlorotrifluoroethylene and the hydrogen with the catalyst.

4. The process according to claim 3 wherein the concentration of chlorotrifluoroethylene in the gaseous stream is comprised between 5 and 55% by volume.

5. The process according to claim 3 wherein the gaseous stream of chlorotrifluoroethylene and hydrogen further comprises an inert gas.

6. The process according to claim 3 wherein the concentration of chlorotrifluoroethylene in the gaseous stream is comprised between 10 and 50% by volume.

* * * * *